United States Patent [19]

Bing

[11] Patent Number: 4,927,629

[45] Date of Patent: May 22, 1990

[54] RELAXATION OF SMOOTH VASCULAR MUSCLE

[75] Inventor: Richard J. Bing, La Canada, Calif.

[73] Assignee: Huntington Medical Research Institutes, Pasadena, Calif.

[21] Appl. No.: 134,034

[22] Filed: Dec. 17, 1987

[51] Int. Cl.$^5$ ............................................. A61K 37/48
[52] U.S. Cl. .................................................. 424/94.6
[58] Field of Search ....................................... 424/94.6

[56] References Cited

U.S. PATENT DOCUMENTS

| | | | |
|---|---|---|---|
| 4,699,919 | 10/1987 | Follet et al. | 514/431 |
| 4,788,304 | 11/1988 | Marshall et al. | 514/885 |
| 4,826,821 | 5/1989 | Clements | 514/78 |

OTHER PUBLICATIONS

Chemical Abstracts, 101:83569v; 86:37623g; 76:121521y; 108:129304e; 108:202449n; 110:5309g; 109:71073f.

Rogausch, H., *Research Experimental Medicine*, (173) (1) (1978), pp. 9–16, abstract only.

*Primary Examiner*—Brian E. Hearn
*Assistant Examiner*—Andrew Griffis
*Attorney, Agent, or Firm*—Ashen Golant Martin & Seldon

[57] ABSTRACT

Certain substances are provided which have the ability to relax smooth vascular muscle, having an endothelial lining, when administered in vitro or by intravenous injection. Examples of useful substances which are pharmaceutically-acceptable include phospholipase $A_2$ ($PLA_2$) and certain lysolecithins. The concentration required is at least about 3 units of $PLA_2$ and at least about $10^{-5}$ Molar lysolecithin. The lysolecithins are dissolved in a suitable solvent, such as dimethyl sulfoxide, for injection. Alternatively, phospholipase $A_2$ is administered directly. The resulting solutions should have a pharmacologically-effective amount of the substance dissolved therein. Importantly, the body does not develop a tolerance to the lysolecithin.

4 Claims, No Drawings

RELAXATION OF SMOOTH VASCULAR MUSCLE

TECHNICAL FIELD

This invention is concerned with a method for relaxing smooth vascular muscle.

BACKGROUND ART

There are a number of conditions which cause the muscle to contract, resulting in adverse reactions in the body. For instance, contraction of coronary arteries can cause severe chest pains, such as those experienced with angina pectoris. In addition, contraction of peripheral vasculature can result in hypertension.

In the case of angina pectoris, a common treatment is the placing of nitroglycerin under the tongue. This produces nitric oxide (NO) which is mediated by cyclic-3',5'-guanosin-monophosphate, resulting in dilation of the coronary arteries and relief of the symptoms. However, the body eventually develops a tolerance to nitroglycerin, thus rendering it ineffective.

There are many agents for treating hypertension but many problems are associated with their use. Some of them cause the patient to develop rashes in some cases. Other cause hypotension unless the dosage is controlled and monitored with great care.

Because of these problems with the agents of the prior art, the discovery of a new class of agents for relaxing smooth vascular muscle is beneficial.

DISCLOSURE OF INVENTION

In accordance with the invention, certain substances are provided which have the ability to relax smooth vascular muscle when administered by intravenous injection. Examples of useful substances which are pharmaceutically-acceptable include phospholipase $A_2$ ($PLA_2$) and certain lysolecithins. The concentration required is at least about 3 units of phospholipase $A_2$ and at least about $10^{-5}$ Molar lysolecithin.

The lysolecithins are dissolved in a suitable solvent, such as dimethyl sulfoxide, while phospholipase $A_2$ may be injected directly. The solutions thus have a pharmacologically-effective amount of the lysolecithin dissolved therein.

Importantly, in contrast to nitroglycerin, the body does not develop a tolerance to the repeated use of the lysolecithin.

BEST MODES FOR CARRYING OUT THE INVENTION

When certain substances are administered to a living body suffering from vascular constriction due to tension in the smooth vascular muscle, the muscle gradually relaxes and normal or improved blood flow is resumed. Such constrictions are found in patients suffering from angina pectoris or hypertension. Unless these constrictions are removed, the patient can suffer serious consequences.

I have discovered that certain substances, which are pharmaceutically-acceptable in phase I experiments at the dosage range listed below, have the desired ability to relax smooth vascular muscle. Preferred substances are certain of the lysolecithins and phospholipase $A_2$. The lysolecithins that may be advantageously employed in the practice of the invention are combinations (esters) of fatty acids, such as palmitic, stearic, oleic, etc. with glycerol, phosphates plus, for example, choline. Most preferred are the stearoyl, palmitoyl, and oleoyl forms of L-α-lysophosphatidylcholine. The lysolecithin is used in a concentration of at least about $10^{-7}$ M and preferably about $10^{-5}$ M.

Phospholipase $A_2$ catalyzes the hydrolysis of the ester bond in position 2 of glycerophospholipids to form a free fatty acid and lysophospholipid, which in turn may be reacylated by acyl-Co-A in the presence of an acyltransferase. Phospholipases split off one fatty acid from a lecithin, converting it into a lysolecithin. Phospholipase $A_2$ is used in a concentration ranging from at least about 3 units up to about 5 units.

The substances utilized in the invention possess a molecular structure comprising a hydrophobic portion within the molecule and a hydrophilic portion at least at one end of the molecule.

Solutions of the lysolecithins in a suitable solvent, such as dimethyl sulfoxide, are administered to patients having the usual symptoms of angina pectoris or hypertension. Phospholipase $A_2$ may be administered directly.

While the concentration and total dosage in patients will vary, depending on the outcome of phase I and II experiments, it appears that the concentrations listed above will generally be pharmacologically-effective.

A single dose of phospholipase $A_2$ of about 3 units will generally produce the desired relaxation in animals in approximately 1 minute. If necessary, a second dose may be administered in approximately two to four hous. With regard to the lysolecithins, the use of the method of the invention does not appear to induce a tolerance in the body, and thus the same dose may be employed as needed, without loss of effectiveness.

Without subscribing to any particular theory, it appears that the effective lysolecithins and phospholipase $A_2$ stimulate cyclic-3', 5'-guanosin-monophosphate for dilating blood vessels. Specifically, in the presence of the endothelial lining of coronary arteries or peripheral vasculature, the substances utilized in the practice of the invention promote relaxation, and thus dilation, of the associated muscle layer. In the body, phospholipase $A_2$ also causes a marked decrease in resistance to blood flow (about 25 to 30%) in coronary arteries and, in some instances, an increase on coronary blood flow.

EXAMPLES

Example 1

A total of 20 rabbits were used; seven aortic strips were obtained from each animal for the study of the effect of lysolecithin and its inhibitors. The effect of lysolecithin was tested by bioassay of rabbit aortic strips suspended in oxygenated Krebs-Henseleit solution at a resting tension of 1.5 g. Male white New Zealand rabbits weighing 2.4 to 3.1 kg were anesthetized with pentobarbital (30 mg/kg) and heparinized with 500 IU/kg I.V. Tracheostomy was performed and the animals were ventilated with a respirator (Bird Mark 10, Space Technology, Palm Springs, CA) to assure sufficient oxygen supply. Median sternotomy was performed and the thoracic aorta was removed and immersed in ice cold Krebs-Henseleit solution. After removal of adjacent superficial connective and adipose tissue, the aorta was cut in rings of about 3 mm in width. These rings were cut into transverse strips. Endothelium was removed by gently rubbing the intimal surface with moistened filter paper wrapped around a wooden stick.

Strips were mounted in an organ chamber of 20 ml capacity with both ends fastened. One end was tied to the bottom of the chamber, while the other end was attached to an isometric pressure transducer (UL-20-Gr, Shinkoh, Minebea Company, Ltd., Tokyo, Japan). The chambers were carefully oxygenated with 95% $O_2$ and 5% $CO_2$ by slow bubbling to prevent foaming. Strips were allowed to equilibrate for 60 minutes, and basal tension of the strips was adjusted to 1.5 g.

Tension development was induced by addition of histamine ($10^{-5}$ M) to the organ chamber. After a steady state was reached, acetylcoline ($10^{-6}$ M) was added. Lysolecithin was dissolved in dimethyl sulfoxide (DMSO) prepared by placing lysolecithin powder (5 mg) in a Watch glass, adding 100 μl DMSO plus 0.5 ml Krebs-Henseleit gradually, and stirring continuously with a glass rod until all solid particles had disappeared. Lysolecithin ($10^{-7}$, $10^{-6}$, and $10^{-5}$ M) in DMSO was then added to the muscle bath. Hemoglobin ($10^{-6}$ and $10^{-5}$ M) or methylene blue ($10^{-5}$ M) were added during lysolecithin induced relaxation, while indomethacin ($10^{-5}$ M) and nordihydroguiaretic acid ($3 \times 10^{-5}$ M) were added prior to precontraction with histamine. Superoxide dismutase (150 U/ml) was administered after the addition of lysolecithin.

Lysolecithin was prepared by phospholipase $A_2$ from egg L-α-phosphatidylcholine, and contained primarily palmitic and stearic acids.

Regarding the effect of lysolecithin on the precontracted unrubbed strip, $10^{-6}$ M lysolecithin resulted in a slight decrease in tension, while $10^{-5}$ M lysolecithin caused a marked decline in tension, comparable to the relaxation induced by $10^{-6}$ M acetylcholine. As compared to the relaxation following acetylcholine, the fall in tension with lysolecithin was more gradual. Both hemoglobin ($10^{-6}$ and $10^{-5}$ M) and methylene blue ($10^{-5}$ M) completely inhibited relaxation. Indomethacin ($10^{-5}$ M) had no effect on relaxation induced by lysolecithin, while nordihydroguiaretic acid partially inhibited relaxation. Relaxation was slightly potentiated by superoxide dismutase. The addition of DMSO alone to the bath had no effect on tension.

In the rubbed strips, the effect of lysolecithin was markedly reduced. The decline in tension was very slight and extended over several minutes. Acetylcholine had no effect on developed tension in the rubbed strip. Hemoglobin did not alter tension, while methylene blue caused a gradual increase.

Example 2

Rabbit aortic strips (4 mm wide), prepared as in Example 1, were subjected to 1.5 g tension, with histamine added to increase tension, as in Example 1. Various lysolecithins were added, to compare the effect of the fatty acid moiety. Relaxation of the lysolecithin was measured as a decline in tension. Hemoglobin ($10^{-5}$ M) was added 20 minutes prior to histamine addition to block relaxation.

The Table below provides a comparison of the effect of the various lysolecithins on relaxation.

TABLE

Effect of Lysolecithin on Relaxation of Vascular Smooth Muscle

| Compound | % Relaxation | Hemoglobin add'n, % Relaxation |
| --- | --- | --- |
| L-α-lysophosphatidyl stearoyl | 51.0 | 92.5 |
| L-α-lysophosphatidyl oleoyl | 58.8 | 104.9 |
| L-α-lysophosphatidyl palmitoyl | 59.5 | 93.2 |
| L-α-lysophosphatidyl caproyl | 88.6 | 96.5 |
| L-α-lysophosphatidyl myristoyl | 100.0 | 112.2 |
| L-α-lysophosphatidyl decanoyl | 95.0 | 108.1 |

In the Table, the addition of histamine is expressed as 100%. Accordingly, the lower the % relaxapalmitoyl lysolecithins are seen to be the preferred compounds.

Thus, there has been provided a method for relaxing smooth vascular muscle. It will be appreciated by those skilled in the art that various changes and modifications of an obvious nature may be made without departing from the spirit and scope of the invention, as defined by the appended claims.

What is claimed is:

1. A method for relaxing smooth vascular muscle comprising administering to a living body having a vascular system with an endothelial lining and suffering from vascular contraction in said smooth vascular muscle an effective amount of a pharmacologically-acceptable amount of prospholipase $A_2$.

2. The method of claim 1 wherein said phospholipase $A_2$ is administered in a concentration of at least about 3 units.

3. The method of claim 2 wherein said phospholipase $A_2$ is administered in a concentration of up to about 5 units.

4. The method of claim 1 wherein said substance is administered by intravenous injection.

* * * * *